United States Patent [19]

Noel et al.

[11] 4,061,016

[45] Dec. 6, 1977

[54] METHOD AND APPARATUS FOR MEASURING THE FOAM LIFE ON AN EFFERVESCENT BEVERAGE

[75] Inventors: Jean Pierre Noel; Gilbert Bauer, both of Strasbourg, France

[73] Assignee: Ste Anonyme Dite Brasseries Kron Enbourg, Strasbourg, France

[21] Appl. No.: 728,401

[22] Filed: Sept. 30, 1976

[30] Foreign Application Priority Data

Dec. 24, 1975 France .................................. 75.40409

[51] Int. Cl.² .......................................... G01N 21/24
[52] U.S. Cl. ..................................... 73/60.1; 141/83; 250/577
[58] Field of Search .................... 73/60.1, 19; 58/39.5, 58/50 R, 74, 75; 141/95, 83; 250/577

[56] References Cited

U.S. PATENT DOCUMENTS

| 176,231 | 4/1876 | Lugrin | 58/74 |
|---|---|---|---|
| 2,380,679 | 7/1945 | Smith | 73/60.1 |
| 3,136,117 | 6/1964 | Speiser | 58/39.5 |
| 3,964,864 | 6/1976 | Dahms | 73/19 X |

FOREIGN PATENT DOCUMENTS

| 765,577 | 8/1967 | Canada | 73/60.1 |
|---|---|---|---|
| R8,072 | 10/1956 | Germany | 73/60.1 |

*Primary Examiner*—Daniel M. Yasich
*Attorney, Agent, or Firm*—Michael J. Striker

[57] ABSTRACT

In order to measure the life of the foam of an effervescent beverage a predetermined quantity of the liquid is held in an upper vessel. This liquid is then allowed to fall rapidly into a lower vessel formed of transparent material and rotated about a vertical axis. As soon as the liquid is poured violently into the lower vessel a timer is started. Simultaneously a light source directs a beam of light upwardly through the vessel and a photocell situated above the vessel receives this light. When the foam has decreased sufficiently to allow the beam to pass through to the photocell, circuitry connected between the photocell and the timer is arrested. The elapsed time is proportional to the life of the head on the beverage.

7 Claims, 5 Drawing Figures

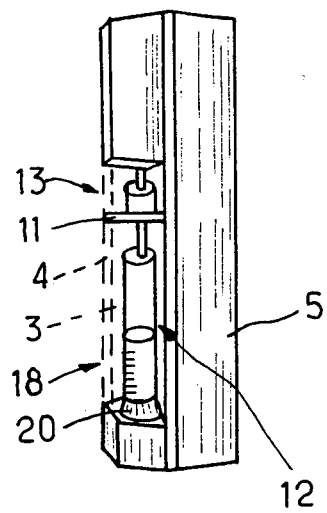
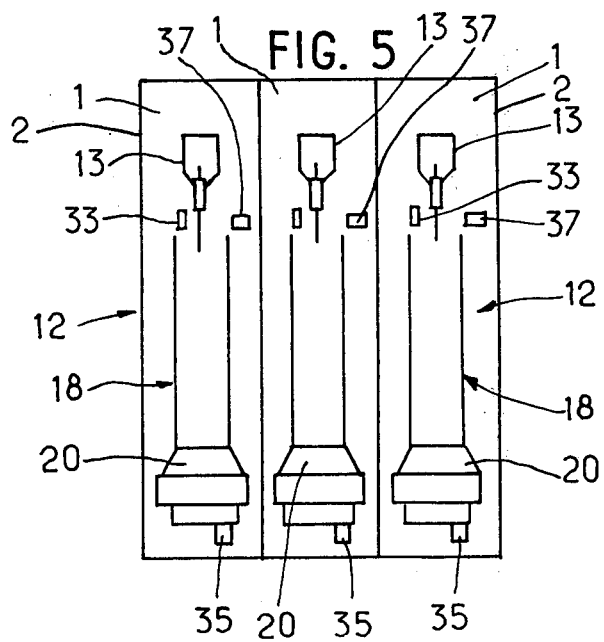
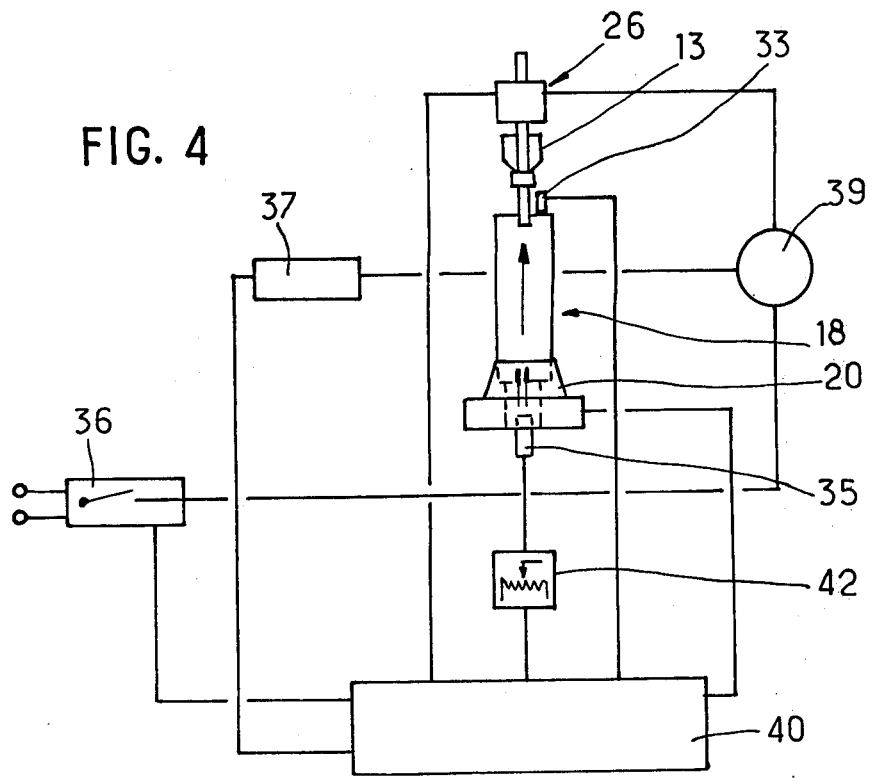

METHOD AND APPARATUS FOR MEASURING THE FOAM LIFE ON AN EFFERVESCENT BEVERAGE

BACKGROUND OF THE INVENTION

The present invention relates to a method of and apparatus for measuring the life of foam on a non-opaque liquid. More particularly this invention is concerned with the measurement of the life of the foam head on an effervescent liquid.

In the manufacture of effervescent beverages, whether artificially carbonated or naturally fermented, it is frequently necessary to know the exact life of the foam on the beverage in order to control the production. This is particularly the case in the brewing of beer where the head is an important aspect of the product, and is also indicative of the effervescence of the product.

In a brewery this is typically done by carefully withdrawing or dipping-out a quantity of beer so as to avoid formation of foam. Then a predetermined quantity of this beer is poured into a graduated vessel and a laboratory assistant times with a stopwatch the interval before the head shrinks to a predetermined level. With this system the considerable difficulty is that it is almost impossible to accurately reproduce the results, as the method of pouring, and the operator's particular sensibilities enter into the measurement of the foam life.

It has been suggested to add a quantity of ground carbon powder to the beer in order artificially to cause the formation of a head on the surface on the quantity of beer. The height of the head thus formed is a good indication of the effervescence of the product. However, this method has the considerable disadvantage that it is almost impossible to reproduce the results accurately, as the exact granularity and density of the carbon powder often change from batch to batch. Furthermore, this system has the disadvantage that it is in effect using an unnatural system for producing the foam, and in addition it renders the beer altogether opaque afterward. Thus, this method has not achieved large commercial success.

A so-called Ross and Clark method allows the relatively accurate determination of the stability of the foam by means of a logarithmic formula. In accordance with this method, a predetermined quantity of beer which has sat for approximately one minute is allowed to pour down into a vessel. As soon as the vessel is filled a stopwatch is started and after a predetermined time a quantity of the beer is removed from the vessel. To the foam that remains in the vessel 2 milliliters of amyl alcohol is added in order to transform this quantity of foam into a predetermined quantity of liquid. In accordance with this method the stability of the foam can be ascertained by the formula:

$$S = \frac{t}{2.303 \log\left[\frac{b+c}{c}\right]}$$

wherein:
$S$ = the stability
$t$ = time the foam is allowed to be reabsorbed,
$b$ = the amount of beer withdrawn, and
$c$ = the volume in milliliters of beer left after addition of the amyl alcohol.

This last-mentioned method gives relatively accurate results, but still it is difficult exactly to reproduce the measuring parameters and similarly it is necessary to use a highly qualified laboratory person to carry out each test. Thus the considerable cost necessary to obtain these measurements is not justified due to their relative inaccuracy.

SUMMARY OF THE INVENTION

It is therefore an object of the present invention to provide an improved method of and apparatus for measuring the life of foam on a nonopaque liquid.

Another object is the provision of an improved system for measuring the life of the head on beer or other effervescent beverages.

These objects are attached according to the present invention in a system wherein a predetermined quantity of liquid to be tested is poured into a vessel so as to cause formation of foam on the surface of the liquid in the vessel. A timer is started substantially when the foam first forms on the surface. A beam of light is directed from one side through the foam and the surface of the liquid and the intensity of the beam is measured on the other side of the surface and of the foam. The timer is stopped when the measured intensity of the beam is greater than a predetermined threshold value. Thus the elapsed time measured by the timer will be indicative of the life of the foam.

With this method it is therefore possible accurately to obtain results with an automatic machine whose readings will have almost entirely eliminated any human factor so that the results obtained can be used in a closely-controlled scientific process.

According to further features of this invention the measuring vessel is formed at least partially of transparent material to allow the light beam to be directed through it. In addition this vessel is rotated about a generally upright axis during the measuring process and the beam of light is directed along a generally vertical path offset from the axis to the vessel. Thus this rotation will tend to even out the foam on the body of nonopaque liquid in the vessel and will, therefore, even further improve the uniformity of the readings obtained.

According to a further feature of the present invention there is provided above the first-mentioned vessel a second vessel formed as a funnel with a downwardly extending outlet tube constituting a conduit that opens above or in the upper region of the first vessel. A plug is provided in the upper end of the tube of the funnel and a solenoid can pull this plug up out of the upper end so as to allow beer in the funnel to rush down through the conduit into the lower vessel. Thus in accordance with this system the beer being tested is carefully dipped out of the production line and gently poured into the upper vessel so as to minimize foam formation. Then the still quantity of beer is dropped through a predetermined height into the lower vessel so that the amount of foaming produced due to the violent fall is always the same.

It is noted that although this present invention refers to the measurement of the life of the head on beer, it is equally suitable for use in any foaming method. In particular it can be used for measuring the foaming of artificially or naturally carbonated softdrinks, of sparkling vines and even for measuring the life of suds produced by detergents.

According to other features of this invention the apparatus has an upright support plate provided on its front side with a pair of horizontal shelf supports the upper of which supports the above-mentioned funnel and the lower of which supports the transparent test vessel. Provided on this vertical support plate is the timer, and on its other side there are provided the various drive motors and control circuits. In addition, shutters or light-blocking plates are provided on the front panel in order to prevent extraneous light from falsifying the readings of teh photocell used to control the timer.

The novel features which are considered as characteristic for the invention are set forth in particular in the appended claims. The invention itself, however, both as to its construction and its method of operation, together with additional objects and advantages thereof, will be best understood from the following description of a specific embodiment when read in connection with the accompanying drawings.

BRIEF DESCRIPTION OF THE DRAWING

FIG. 3 is a side perspective view of the apparatus of FIGS. 1 and 2;

FIG. 4 is a largely schematic view illustrating the controller for the apparatus of FIGS. 1 – 3; and FIG. 5 is a largely schematic front view illustrating how three units according to this invention can be united in one assembly.

SPECIFIC DESCRIPTION OF A PREFERRED EMBODIMENT

Figure 1:
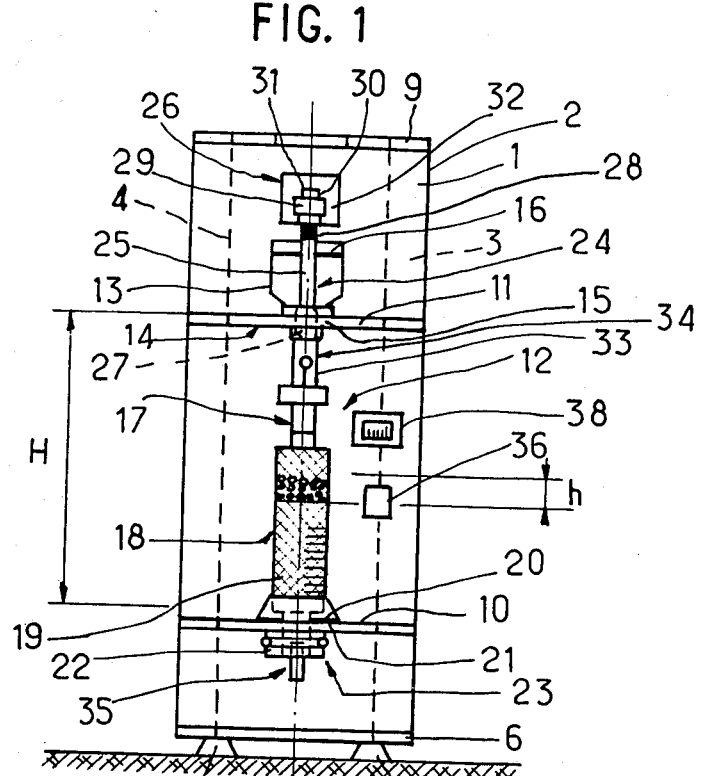
FIGS. 1 and 2 are front and back elevational views, respectively, of the apparatus according to this invention.
Figure 2:
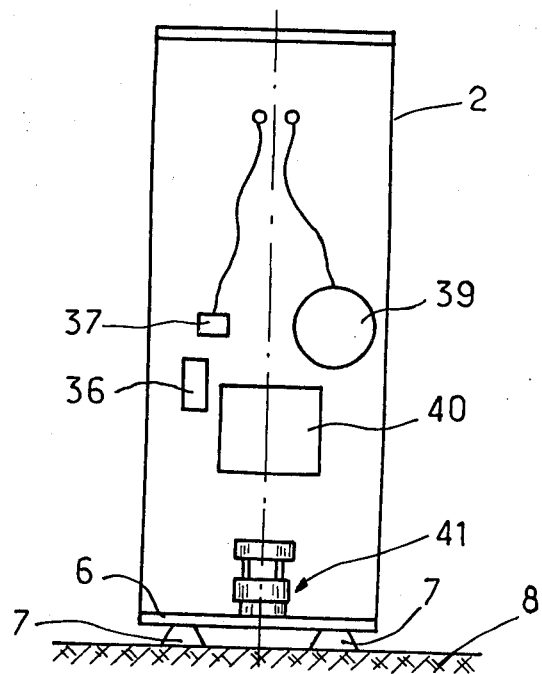

As shown in FIGS. 1 – 4 the testing apparatus according to this invention has a housing 1 constituted by a vertical support plate 3 provided with two forwardly extending and vertical plates 3 and 4 which tend to block the entrance of extraneous light. In addition this frame 1 is closed at its back by a cover plate 5 and has a lower support 6 provided with feet 7 adapted to support the arrangement on the ground 8. The top of the housing 1 is provided with a top plate 9 and a pair of horizontal shelf supports 10 and 11 are provided on the front of the plate 2.

A pouring assembly 12 is supported on these shelves 10 and 11 and comprises an upper glass funnel 13 having a downwardly extending tubular neck 17 and sitting by means of a resilient washer 14 on the upper surface 15 of the shelf 11. The funnel 13 is provided with at least one level-indicating indicia 16 that indicates a predetermined volume within the funnel.

Provided below the funnel in line with the neck 17 thereof is a transparent glass measuring vessel 18 of cylindrical shape and provided with an asbestos insulating and light-blocking sheathing 19 around its outside. The flat bottom of the vessel 18 rests in an annular base 20 which sits on a support 21 constituting a turntable which extends down through the shelf 10 and is formed at a lower region 22 with a peripheral groove that allows it to operate as a turntable 23. A motor 41 on the back of the plate 2 is connected via an elastic drive belt to a groove in the portion 22 to rotate the vessel 18 about an upright axis that is also the axis of the funnel 13. The element 21 is smoothly journalled in the shelf 10 and sufficiently greased so that it allows smooth non-vibrational rotation of the element 18.

The funnel 13 is provided with a valve 24, constituted by a vertical rod 25 which has a lower end 27 that can snugly fit in and block the upper end of the tube 17 and an upper end 31 passing through a square hole 30 in a coil 29 in a solenoid 36 attached to the plate 2. Only the upper portion 28 of rod 25 is ferromagnetic, the lower portion of the rod 25 being glass and the lower end being ground so as to form a fluid-tight seal with the tube 17.

Provided below the shelf 10 is a light source 35 of monochromatic or polarized light which directs a beam upwardly through the vessel 18 and liquid and foam therein along a path offset from the rotation axis of this vessel 18. Similarly offset from the axis in a light-screening tube 34 is a photocell 33 connected to a controller 40 of the apparatus.

In addition the apparatus is provided on the front of its vertical plate 2 with an elapsed-time indicator 38 and a start-stop switch 36. As better shown in FIG. 4 the start-stop switch controls a pulse generator 39. Furthermore, the light source 35 is shown to be connected via a potentiometer 42 to the controller 40. The on-off switch 36 is connected to a conventional power source, and a pulse counter 37 having the elapsed-time indicator 38 is connected to the pulse generator 39.

In use the device functions as follows:

A quantity of beer is gently dipped out of the production facilities with minimal foam formation and is gently poured into the funnel 13 up to the mark 16. Then the switch 36 is operated so as simultaneously to start the pulse generator 39 and to energize the solenoid 26. This causes the beer to rush down in the tube 17 and all violently in the vessel 18 which is meanwhile rotating continuously about the vertical axis.

Meanwhile the light 35 is directing its beam upwardly into the vessel 18. So long as the head is relatively thick, however, all of the light of the source 35 will be deflected and refracted within the vessel 18 and will only be sensed at a very low intensity by the photocell 33. Since the beer has dropped through an accurately determined height H a predetermined level h of foam will form on the surface of the beer. The rotation of the vessel 18 will cause this foam to be smoothly distributed over the entire surface of the beer. Even when the foam is lessened sufficiently that only a ring is left around the inside of the vessel, driven outwardly centrifugally, the photocell receiver 33 will still receive light from the source 25 only at a very low intensity. Finally when the intensity of the light received exceeds a predetermined threshold value, the controller 40 stops the pulse generator 39, so that the pulse counter 37 similarly stops. The elapsed time can then be read on the display 38. The vessel 18 may then be emptied and another test carried out.

It is noted that with this system it is possible to control the threshold level most easily by varying the potentiometer 42, which itself could be replaced by a simple phase-angle power control.

FIG. 5 indicates how three such devices can be manned right next to other in order to allow large-scale testing of beer or any similar product.

It will be understood that each of the elements described above, or two or more together, may also find a useful application in other types of apparatus differing from the types described above.

While the invention has been illustrated and described as embodied in a beer head tester, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A method of measuring the life of foam on a nonopaque liquid, said method comprising the steps of:
   selectively pouring a predetermined quantity of said liquid from a preselected height into a vessel to cause formation of a predetermined level of foam on the surface of the liquid of the vessel;
   rotating said vessel continuously on a support about a generally vertical axis and thereby rotationally entraining said liquid and said foam;
   starting a timer substantially when said foam first forms on said surface;
   directing a beam of light generally vertically and offset from said axis from one side through said foam and said surface as same rotate;
   measuring the intensity of said beam on the other side of said surface and said foam; and
   stopping said timer when the measured intensity of said beam is greater than a predetermined threshold level, whereby the elapsed time between starting and stopping of the timer is indicative of the life of said foam.

2. The method defined in claim 1, further comprising the step of gently filling said quantity of liquid into a second vessel different from the first-mentioned vessel and thereafter pouring said quantity from said second vessel violently into said first vessel.

3. The method defined in claim 1 wherein said liquid is an effervescent beverage.

4. An apparatus for measuring the life of foam on a nonopaque liquid, said apparatus comprising:
   a support;
   a vessel having at least one transparent wall;
   means for selectively pouring a predetermined quantity of said liquid into said vessel in such a manner that a predetermined depth of foam forms on the surface of said liquid;
   means for rotating said vessel about a generally vertical axis on said support and thereby rotationally entraining said liquid and said foam;
   a timer;
   means connected between said timer and said means for pouring for starting said timer when said quantity is poured into said vessel;
   means including a light source for directing a beam of light generally vertically and along a path offset horizontally from said axis through said wall, said surface, and said foam; and
   means aligned with said light source and connected to said timer for arresting said timer when the intensity of said beam after passage thereof through said surface and said foam exceeds a predetermined limit.

5. The apparatus defined in claim 4 wherein said means for pouring includes a second vessel generally above the first-mentioned vessel, a conduit between said vessels, and a valve in said conduit, whereby opening of said valve allows liquid in said second vessel to flow downwardly through said conduit into said first vessel.

6. The apparatus defined in claim 5 wherein said second vessel is funnel-shaped and has a downwardly extending small-diameter outlet tube constituting said conduit.

7. The apparatus defined in claim 6 wherein said valve is a vertically reciprocal plug engageable in the upper end of said tube and a solenoid connected to said plug for vertically reciprocating same.

* * * * *